United States Patent [19]
Kokawa et al.

[11] Patent Number: 6,137,115
[45] Date of Patent: Oct. 24, 2000

[54] FILM INSPECTING APPARATUS

[75] Inventors: Ryohei Kokawa; Yasuhiro Yamakage, both of Hadano; Makoto Shinohara, Isehara, all of Japan

[73] Assignee: Shimadzu Corporation, Kyoto, Japan

[21] Appl. No.: 09/233,472

[22] Filed: Jan. 20, 1999

[30] Foreign Application Priority Data

Feb. 26, 1998 [JP] Japan .................................. 10-045092

[51] Int. Cl.$^7$ ................................................. G01N 21/86
[52] U.S. Cl. .................. 250/559.4; 250/559.41; 250/559.39; 356/237; 356/237.2; 356/335; 356/376; 356/394
[58] Field of Search ........................... 250/559.4, 559.39, 250/559.41, 559.44, 559.45; 356/237, 237.2, 335, 336, 376, 379, 371, 394, 430; 382/141, 261

[56] References Cited

U.S. PATENT DOCUMENTS 5,572,320  11/1996  Reintjes et al. ........................ 356/335
5,923,430   7/1999  Worster et al. ........................ 356/394
5,963,314  10/1999  Worster et al. ...................... 356/237.2

*Primary Examiner*—Loha Ben
*Attorney, Agent, or Firm*—Kanesaka & Takeuchi

[57] ABSTRACT

A film inspecting apparatus is used for inspecting fine roughness and particle state on a surface of a thin film. In inspecting the thin film surface, shape data of the thin film are obtained by a scanning type probe microscope. The obtained shape data are analyzed to identify individual particles, and the fine roughness and particle state on the thin film surface are inspected based on the particle data obtained by the shape data analysis. The film inspecting apparatus includes a particle analyzing device for inspecting the fine roughness and particle state on the thin film surface by using the shape data obtained by the scanning type probe microscope. The particle analyzing device includes a particle extracting device for extracting the particles on the film surface from the shape data, and a particle data calculating device for calculating the particle data based on the data extracted by the particle extracting device.

7 Claims, 3 Drawing Sheets

FILM INSPECTING APPARATUS

BACKGROUND OF THE INVENTION AND RELATED ART STATEMENT

The present invention relates to a film inspecting apparatus, in particular, a film inspecting apparatus using a scanning type probe microscope.

For a hard disc and semiconductor device, a thin film, such as a dielectric film, has been often used. In forming the thin film, surface roughness and quality of the thin film are important elements, and control of the film quality is important in controlling a quality of the semiconductor device, which influences the precision and yield of the semiconductor. For example, in case a wiring portion of the semiconductor device is formed of a thin film, electrical characteristics thereof greatly vary according to the surface roughness and quality of the thin film.

Especially, as the semiconductor device is finely structured, the surface roughness and particle size required for the surface of the thin film also become finer. Therefore, even if the thin film has the surface roughness and particle size which have not conventionally influenced the quality of the semiconductor device, proper attention has to be paid thereto.

Heretofore, a roughness measuring gauge for measuring roughness of an object's surface has been known. However, a range of the roughness measured by the roughness measuring gauge is large, and the roughness measuring gauge is not sufficient for measuring an unevenness of the surface of the thin film in the order of a nanometer.

Also, generally, a scanning type probe microscope (SPM), such as an interatomic force microscope (AFM) and a scanning type tunnel microscope (STM), has been known. However, in such a scanning type probe microscope, only a shape of the surface can be obtained as three-dimensional data, wherein the surface shape can be obtained as a continuous uneven shape, and the particle state for forming the thin film surface can be recognized.

Therefore, it is impossible by the scanning type probe microscope to recognize individual particles on the surface of the thin film in order to inspect the sizes and states of the particles.

Thus, any useful means for inspecting the fine roughness and the particle state on the surface of the thin film have not substantially been presented, and a film inspecting apparatus for measuring such fine roughness and particle state of the thin film has been strongly requested.

Accordingly, an object of the invention is to obviate the problems of the prior art and to provide a film inspecting apparatus, wherein fine roughness and particle state on a surface of a thin film can be obtained and inspected.

Further objects and advantages of the invention will be apparent from the following description of the invention.

SUMMARY OF THE INVENTION

In the present invention, shape data of a thin film are obtained by a scanning type probe microscope; the obtained shape data are analyzed to distinguish respective particles; and fine roughness and particle states on a surface of the thin film are inspected through the analyzed particle data.

The film inspecting apparatus of the invention includes particle analyzing means for inspecting the fine roughness and the particle states on the surface of the thin film by using the shape data obtained through the scanning type probe microscope. The particle analyzing means is formed of particle extracting means for extracting particles on the film surface from the shape data, and particle data calculating means for calculating particle data relating to the particles based on the data extracted by the particle extracting means.

Incidentally, the shape data obtained by the scanning type probe microscope are three-dimensional data for showing a surface shape of an object to be inspected, i.e. data obtained as a continuous uneven surface. Under the shape data, it is impossible to obtain the particle states forming the surface of the thin film.

The particle extracting means is to carry out a first step of the particle analysis, wherein there is carried out a data processing for distinguishing and extracting the respective particles constituting the surface of the film from the shape data showing the continuous surface shape.

Also, the particle data calculating means is to carry out a second step of the particle analysis, wherein a data processing is executed to calculate the particle data relating to the particles based on the data extracted by the particle extracting means. In the particle data calculating means, characteristic quantities for distinguishing the respective particles and statistics comprising plural particles from the respective characteristic quantities are calculated as the particle data.

Incidentally, the characteristic quantities include a center of gravity in the X axial direction, center of gravity in the Y axial direction, absolute maximum diameter, pattern width, horizontal fillet diameter, vertical fillet diameter, radius corresponding to a circle, average radius, dispersion of average radii, peripheral length, enveloping peripheral length, maximum value of Z (in the height direction), average value of Z (in the height direction), area except for holes, area including holes, surface area, volume, pattern direction, spindle angle of two-dimensional moment of inertia, occupancy percentage, area percentage, oblateness, degree of roundness, degree of unevenness and degree of a needle shape, of each particle. The statistics include a minimum value, particle number of the minimum value, maximum value, particle number of the maximum value, range, average value, standard deviation, total value, number of particles and the like.

In the present invention, the shape data obtained from the scanning type probe microscope are inputted in the film inspecting apparatus, or have been inputted beforehand. In the particle extracting means of the particle analyzing means, the shape data are processed to obtain extraction data through extraction of the respective particles on the film surface. Next, in the particle data calculating means of the particle analyzing means, the extraction data are processed for calculating the characteristic quantities relating to the respective particles, and the calculated characteristic quantities are processed to obtain the statistics.

The characteristic quantities and the statistics obtained by the particle analyzing means are data characterizing the particles on the film surface. Therefore, different surfaces of an object to be inspected or particles of different objects to be inspected are compared, so that the fine roughness and the particle states on the surface of the thin film can be inspected.

Also, the other data relating to the film are added to the particle data, and by using these data, comparison and inspection of the film may be carried out.

In the film inspecting apparatus according to the invention, the inspection is carried out based on the shape data of the thin film obtained by the scanning type probe microscope. Therefore, the film inspecting apparatus of the invention may be combined with the scanning type probe microscope in its structure, or may be separated from the scanning type probe microscope so that only the detected data are inputted therein.

Therefore, according to the film inspecting apparatus of the invention, the fine roughness and particle states on the surface of the thin film in the order of a nanometer can be inspected by separating and extracting the respective particles, and obtaining the characteristic quantities and the statistics of the respective particles.

DETAILED DESCRIPTION OF PREFERRED EMBODIMENTS

Hereunder, an embodiment of the present invention is explained with reference to the accompanying drawings.

Figure 1:
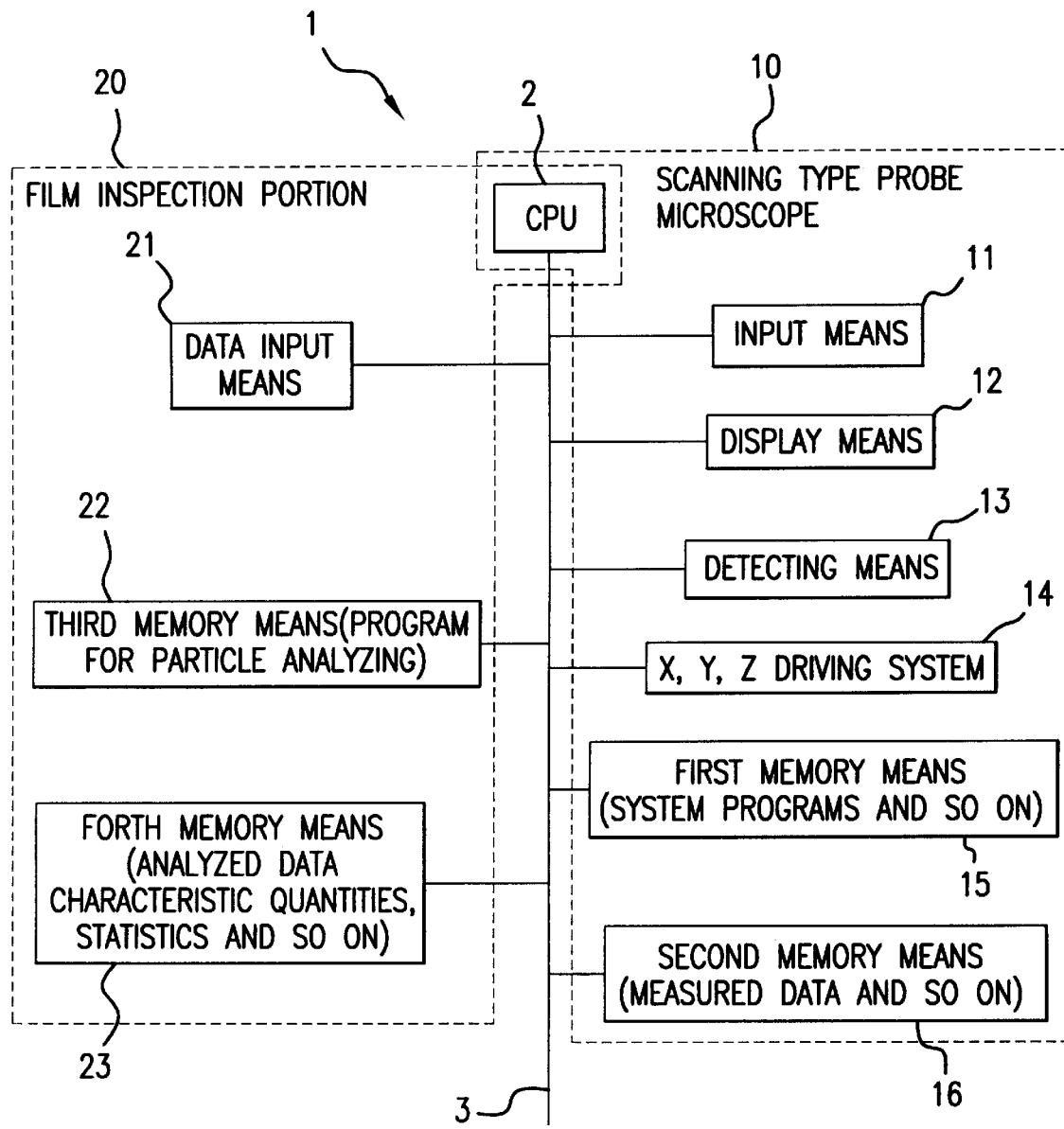
FIG. 1 is a block diagram of an embodiment of a film inspecting apparatus of the invention.

FIG. 1 is a block diagram for showing a structure of a film inspecting apparatus according to the present invention. Incidentally, FIG. 1 shows a structure wherein the film inspecting apparatus is combined with a scanning type probe microscope. In FIG. 1, the film inspecting apparatus 1 includes a scanning type probe microscope 10 and a film inspection portion 20, and the respective elements are connected with each other through a bus 3 to be processed by CPU 2.

The scanning type probe microscope 10 may be formed of a scanning type tunnel microscope STM and an interatomic force microscope AFM. In the scanning type tunnel microscope STM, a probe is allowed to approach a surface of a sample so that the probe or the sample can be moved in a three-dimensional direction; and a distance between the sample surface and the probe is controlled in the order of a subnanometer so that a tunnel current flowing between the probe and the sample surface becomes constant. Thus, a three-dimensional shape is measured with a resolving power at an atomic level, and an atomic arrangement on the surface of the sample and a surface shape of the sample are observed. Also, the interatomic force microscope AFM includes a probe, a cantilever for supporting the probe and a displacement measuring system for detecting a curvature of the cantilever. The interatomic force microscope AFM detects an interatomic force, such as an attracting force or repulsive force, between the probe and the sample to observe a shape of the sample surface by controlling the interatomic force to be constant.

Hereunder, a general structure of a scanning type probe microscope 10, as shown in FIG. 1, including the scanning type tunnel microscope STM and the interatomic force microscope AFM, is explained.

The scanning type probe microscope 10 includes detecting means 13, such as a current measuring system and a displacement measuring system, for detecting the shape of the sample surface; and an X, Y, Z driving system 14 for displacing the sample or the probe in the detecting means 13. The detecting means 13 and the X, Y, Z driving system 14 are controlled by a system program for controlling the whole scanning type probe microscope stored in the first memory means 15, such as ROM, and the CPU 2. Detected data, i.e. shape data on the sample surface, can be stored in the second memory means 16, such as RAM.

Also, the scanning type probe microscope 10 can be operated through input means 11, and measured states and detected results are displayed in display means 12.

A film inspection portion 20 includes third memory means 22, such as ROM, for storing a particle analyzing program to analyze particles; and fourth memory means 23, such as RAM, for storing the data obtained by the analysis. Particle analyzing means can be constituted by the particle analyzing program and the CPU 2.

The particle analyzing program includes a particle extracting program for extracting the particles on the film surface from the shape data, and a particle data calculating program for calculating particle data relating to the particles based on the extracted data. By executing the respective programs through the CPU 2, particle extracting means and particle data calculating means are constituted.

The particle extracting program is a program to execute a data processing for extracting a shape from the shape data, wherein by judging existence of the shape from the shape data and further discriminating or identifying the shape from other shapes, boundary lines among the particles and crystal grains from a continuous uneven shape are distinguished to extract the respective particles.

Also, the particle data calculating program executes data processings for calculating characteristic quantities with respect to the respective particles by using the extracted data, and for calculating statistics by using the obtained characteristic quantities. Also, in the film inspection portion 20, other data can be stored in the fourth memory means 23 through the data input means 21.

In the data processing according to the particle analyzing program, in case the particles are extracted, the shape data are taken from the second memory means 16 to execute the extraction processing, and the extracted data are stored in the fourth memory means 23. Also, in case the particle data are calculated, the extracted data are taken from the fourth memory means 23 to execute a calculation processing, and the calculated data of the characteristic quantities and the statistics are stored again in the fourth memory means 23.

Incidentally, in FIG. 1, the first memory means and the third memory means are separated for an explanation purpose of functions, but they may be provided in the separated storing areas in the same memory means. Also, the second memory means and the fourth memory means are separated for an explanation purpose of functions, but they may be provided in the separated storing areas in the same memory means, as well.

Figure 2:
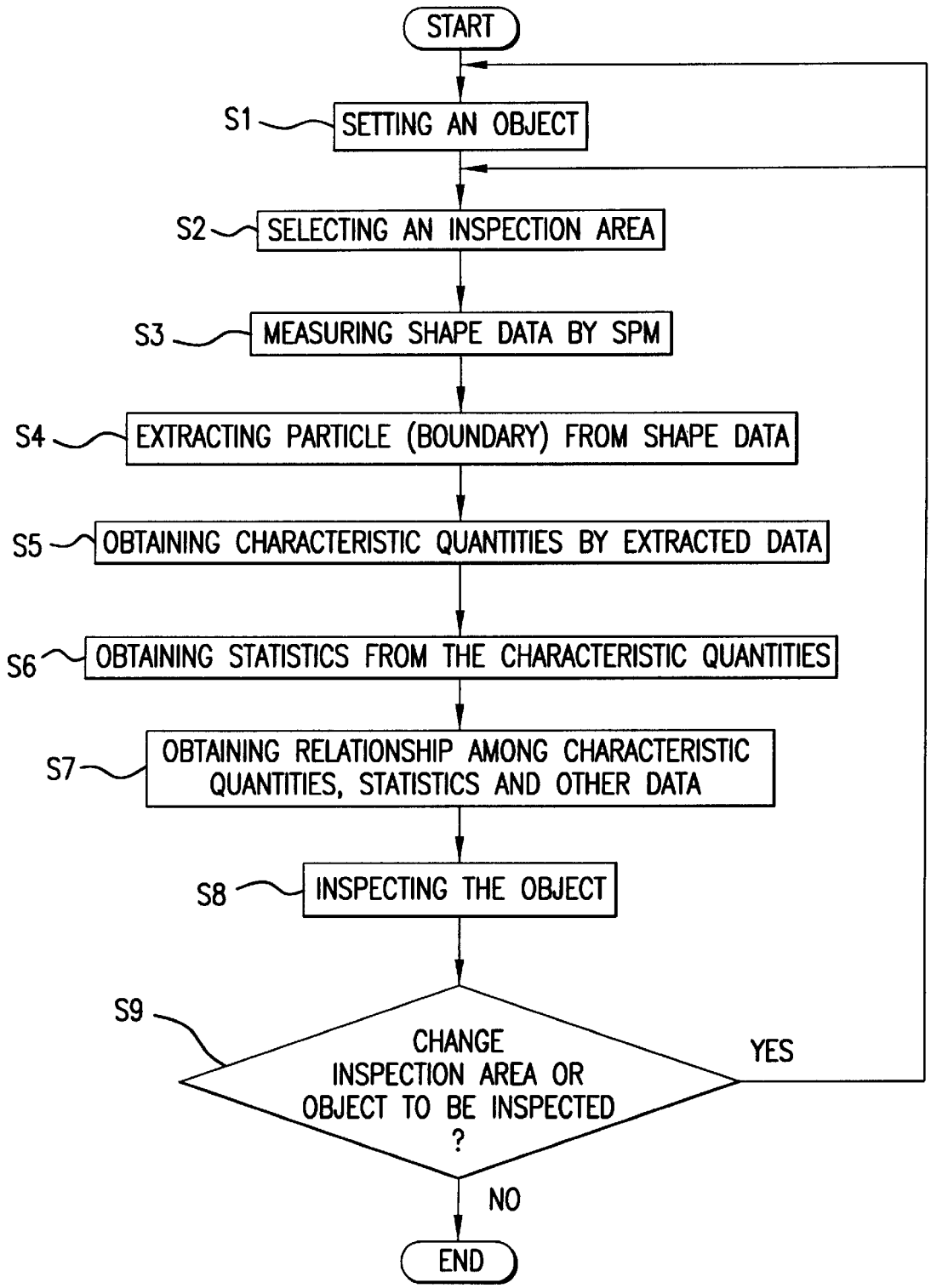
FIG. 2 is a flow chart for explaining an operation of the film inspecting apparatus of the invention.
Figure 3A:
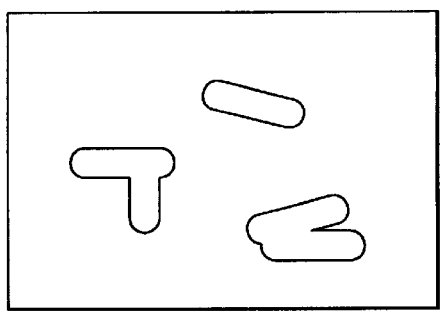
FIGS. 3a and 3b are image displays of the three-dimensional data for explaining an operation of the film inspecting apparatus of the invention.
Figure 3B:
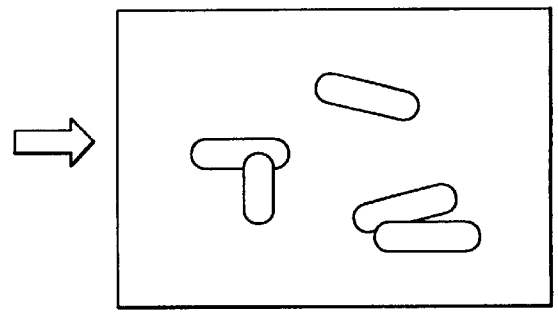
Figure 4A:
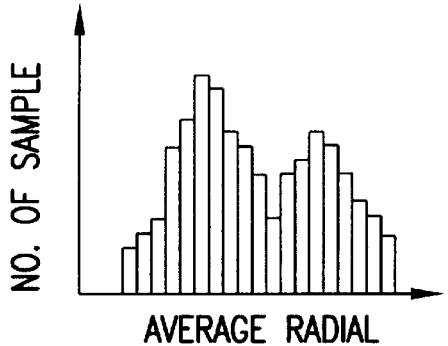
FIGS. 4a and 4b are graphs showing the particle data obtained by the film inspecting apparatus of the invention.
Figure 4B:
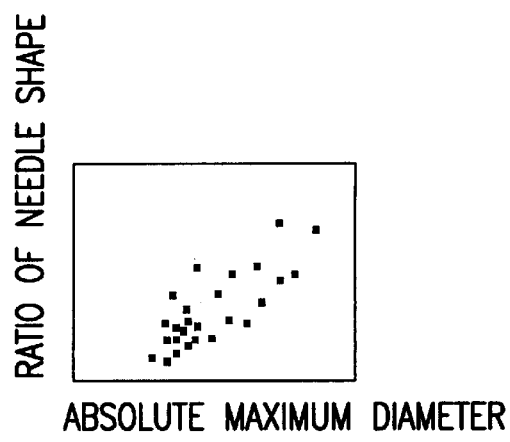
Figure 5:
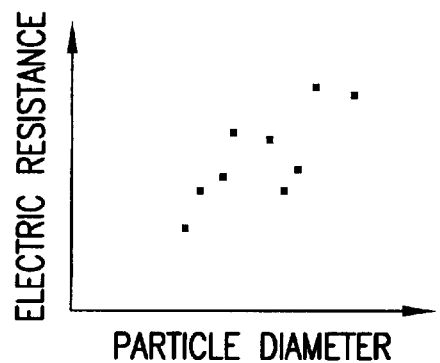
FIG. 5 is a data relation graph showing a relationship between the particle data obtained by the film inspecting apparatus of the invention and other data.

Next, an operation of the film inspecting apparatus 1 according to the present invention is explained with reference to the flow chart of FIG. 2, three-dimensional data drawings of FIGS. 3a and 3b, statistic drawings of FIGS. 4a and 4b, and a data relation drawing of FIG. 5.

An object to be inspected is set on a scanning type probe microscope (Step S1), and an inspection area is selected (Step S2). In the selection of the inspection area, an image obtained by an optical microscope provided to the scanning type probe microscope and the shape data obtained beforehand through a measurement are displayed on the display means 12, and the inspection area can be selected by moving the display area by the input means 11.

The shape data over the selected inspection area are measured by the scanning type probe microscope 10 (Step S3), and the measured shape data are stored in the second memory means 16. The shape data are the three-dimensional data of the surface shape of the object to be inspected. FIG. 3a is a schematic diagram, as image data, of the shape data obtained by the scanning type probe microscope 10. In the shape data obtained by the scanning type probe microscope 10, the boundary lines between the adjacent particles or crystal grains are not distinguished, and they are recognized as a continuous material.

In the film inspection portion 20, the shape data are read out from the second memory means 16 by using the particle extraction program stored in the third memory means 22 to execute the particle extraction process (Step S4). The extracted data are stored in the fourth memory means 23. FIG. 3b is a schematic diagram, as image data, of the extracted data after the particle extraction processing is carried out. In the extracted data, the boundary lines between the adjacent particles or crystal grains can be distinguished, and the respective particles are recognized individually.

In the film inspection portion 20, by using a particle data calculating program stored in the third memory means 22, the extracted data are read out of the fourth memory means 23 to execute a calculation processing of the characteristic quantities (Step S5). The calculation processing to be executed may also be designated by the input means 11. The calculated characteristic quantities are stored in the fourth memory means 23. Also, the calculated characteristic quantities may be displayed on the display means 12. FIGS. 4a, 4b are graphs showing the characteristic quantities. The characteristic quantities to be displayed can be designated by the input means 11.

Also, in the film inspection portion 20, by using the particle data calculating program stored in the third memory means 22, the characteristic quantities are read out from the fourth memory means 23, and the calculation processing of the statistics is executed (Step S6). The calculating program to be executed may be designated by the input means 11. The calculated characteristic quantities are stored in the fourth memory means 23. Also, the calculated statistics may be displayed on the display means 12 or the like. The statistics to be displayed can be designated by the input means 11.

Further, in the film inspection portion 20, other data, such as electric resistance, may be inputted from the data input means 21, and stored in the fourth memory means 23. A relationship among the inputted other data, the characteristic quantities and the statistics is obtained (Step S7), and is displayed on the display means 12. From the display, a relationship between the surface shape and the physical characteristics is examined, and a thin film and a semiconductor device having the thin film can be inspected. An electric resistance is inputted as the other data, and a graph showing a relationship between the calculated particle diameters and electric resistances can be obtained as shown in FIG. 5.

By using a relationship among the characteristic quantities, statistics and other data, the object is inspected (Step S8), and in case the inspection area is changed, the process is returned to the Step S2, or in case the object to be inspected is changed, the process is returned to the Step S2 (Step S9).

As described above, according to the film inspecting apparatus of the present invention, fine roughness and particle states of the thin film surface can be inspected.

While the invention has been explained with reference to the specific embodiment of the invention, the explanation is illustrative and the present invention is limited only by the appended claims.

What is claimed is:

1. A film inspecting apparatus comprising:

means for obtaining shape data on a film, and particle analyzing means electrically connected to the shape data obtaining means, said particle analyzing means including particle extracting means for extracting particles on the surface of the film from shape data obtained by the shape data obtaining means, and particle data calculating means for calculating particle data relating to particles based on data extracted by said particle extracting means so that characteristics on the surface of the film are inspected.

2. A film inspecting apparatus according to claim 1, wherein said particle extracting means judges based on the shape data if there are shapes on the surf ace of the film and identifies the shapes different from each other to identify boundaries of the particles.

3. A film inspecting apparatus according to claim 2, wherein said particle data include characteristic quantities for identifying the respective particles, and statistics based on the characteristic quantities.

4. A film inspecting apparatus according to claim 3, wherein said characteristic quantities include, in each particle, a center of gravity, absolute maximum diameter, pattern width, horizontal fillet diameter, vertical fillet diameter, radius corresponding to a circle, average radius, peripheral length, enveloping peripheral length, maximum value in a height direction , average value in the height direction, area except for holes, area with holes, surface area, volume, pattern direction, spindle angle of two-dimensional moment of inertia, occupancy percentage, area percentage, oblateness, degree of roundness, degree of unevenness and degree of a needle shape.

5. A film inspecting apparatus according to claim 3, wherein said statistics include a minimum value, particle number of the minimum value, maximum value, particle number of the maximum value, range, average value, standard deviation, total value, number of particles.

6. A film inspecting apparatus according to claim 3, wherein said means for obtaining shape data is a scanning type probe microscope obtaining a shape of the surface as three-dimensional data.

7. A film inspecting apparatus according to claim 6, wherein said scanning type probe microscope includes input means, display means and detecting means connected to each other, said input means operating the scanning type probe microscope said display means displaying the characteristic quantities and statistics, and said detecting means detecting the shape of the surface of the film.

* * * * *